United States Patent [19]

Mountford

[11] Patent Number: 4,981,045
[45] Date of Patent: Jan. 1, 1991

[54] TESTING OF LIQUID MELTS AND PROBES FOR USE IN SUCH TESTING

[75] Inventor: Norman D. G. Mountford, Toronto, Canada

[73] Assignee: The University of Toronto Innovations Foundation, Toronto, Canada

[21] Appl. No.: 393,060

[22] Filed: Aug. 10, 1989

[30] Foreign Application Priority Data

May 17, 1984 [CA] Canada .................................. 454623

Related U.S. Application Data

[60] Continuation of Ser. No. 114,023, Oct. 28, 1987, abandoned, which is a division of Ser. No. 826,149, Jan. 17, 1986, Pat. No. 4,770,699.

[51] Int. Cl.$^5$ .......................................... G01N 24/00
[52] U.S. Cl. ...................................... 73/644; 73/61 R
[58] Field of Search ............... 73/592, 644, 661, 61 R, 73/61 LM; 75/93 R

[56] References Cited

U.S. PATENT DOCUMENTS

| | | | |
|---|---|---|---|
| 3,444,726 | 5/1969 | Young et al. ................... | 73/61 R |
| 3,585,865 | 6/1971 | Bungart et al. .................. | 73/71.5 |
| 4,261,197 | 4/1981 | mansfield ........................ | 73/61 R |
| 4,287,755 | 9/1981 | Mansfield ........................ | 73/61 R |
| 4,373,950 | 2/1983 | Shingu et al. ................... | 75/68 R |
| 4,662,215 | 5/1987 | Eckert ............................. | 73/644 |

OTHER PUBLICATIONS

"Acoustic Methods", by V. M. Lantukh, et al., 2418 The Soviet Journal of NDT, vol. 15, May 1979, No. 5, pp. 404–410.
"Precipitation Effects in Liquid Aluminum Alloys", by N. D. Mountford et al. Journal of the Institute of Metals 1959, vol. 88, pp. 121-127.

*Primary Examiner*—John Chapman
*Assistant Examiner*—Louis M. Arana
*Attorney, Agent, or Firm*—Fleit, Jacobson, Cohn, Price, Holman & Stern

[57] ABSTRACT

A probe for ultrasound testing or treatment of a molten metal is provided. The probe includes an ultrasound transmitting rod having a downstream end adapted to contact molten metal under test or treatment. A piezoelectric crystal is provided on the probe and is adapted to supply ultrasound to or receive ultrasound from the rod. A rod cooling station is located near the downstream end of the rod and is operable to create in the rod, a steep temperature gradient at least equivalent to 700° C. over a length of 50 mm from the point of melt contact for a cylindrical steel rod 25 mm in diameter when the probe is in contact with the molten metal at melt temperature. A method of testing a liquid molten melt is also provided.

13 Claims, 4 Drawing Sheets

TESTING OF LIQUID MELTS AND PROBES FOR USE IN SUCH TESTING

This application is a continuation of application Ser. No. 07/114,023, filed Oct. 28, 1987 now abandoned, which is a divisional of application Ser. No. 826,149, filed Jan. 17, 1986, now P.N. 4,770,699.

This invention relates to processes and apparatus for testing molten metals. More particularly, it relates to testing batches of molten metals (hereinafter described as "metal melts") such as aluminium, ferrous metals such as cast iron and steel, nickel, cobalt, titanium, copper and alloys, by acoustic techniques, to determine the quality, purity etc. of the batch.

It is known to use an ultrasonic technique to investigate the presence of oxides and precipitated phases in melts of aluminium alloys. This is described in a paper by N.D.G. Mountford and R. Calvert, "Journal of the Institute of Metals", 1959-60, Volume 88, pages 121-127. This work demonstrated that the quality of liquid aluminium alloys could be studied and such effects as peritectic reactions could be measured in relation to their equilibrium conditions. A recent technique embodying an improved transducer has been set up, and quantitative measurement electronics have been very successful in registering the efficiency of filters.

A principal difficulty in conducting techniques for studying the quality of molten metals is caused by the solid/liquid interface where a sound-emitting probe enters the melt. At such a location, the sound must be transmitted across a liquid-solid interface. Then, to receive and analyse the sound reflections or echoes, these reflections must be transmitted back across a liquid-solid interface, to a receiver probe, for analysis. In previous work with aluminium metal, it has been common practice to use separate transmitting probes and receiving probes. In other cases, a single probe is used both as transmitter of ultrasound pulses to the melt and as receiver of reflections therefrom. Unless the interference with the sound waves caused by the liquid/solid interfaces can be reduced to a sufficiently low value, the interference is likely to mask any reflections obtained from, say, inhomogeneities, impurity particles, air pockets and cavities in the melt. Analysis of the composition of the melt from the reflected signals is thus made impractical.

To reduce the problem of interference at the interface, it has been suggested that the same base metal as the alloy to be examined should be used for the transmission probe. This provides very similar densities and speed of sound in the liquid and solid media, giving rise to good acoustic impedance matching.

In the case of steel probes used for examining steel melts, in which the speed of sound is 5.8 mm/sec, the density is 7800 kg/m$^3$, and thus the acoustic impedance ($Z_s$) is 45.24. For liquid steel, experiments have shown the speed of sound therein to be 5.2 mm/sec and the density approximately 7100 kg/m$^3$, giving an acoustic impedance of 36.92. From these figures, it can be calculated that only about 1% of the sound is reflected at the interface. The main problem in using a probe with such an interface is the maintenance of the interface itself, in a stable condition. This can be overcome by enclosing the molten end in some form of ceramic sleeve, but then the actual position of the liquid-solid interface within the sleeve is determined by the rate at which heat can be abstracted by the probe, and by the thermal conductivity of the steel itself.

It is desirable to use steel for the construction of an ultrasound probe, because of its cheapness and high melting point, especially when testing or treating a ferrous metal melt.

The present invention provides a novel probe for transmission of ultrasound pulses to a molten metal and reception of sound reflection therefrom, in which the ultrasound pathway through very high temperature metal of the probe is reduced to a very small length. This is accomplished by providing the probe with a cooling means near to the melt-penetrating end thereof. The cooling means is effective in use to ensure that reflected sound waves from the melt do not travel for a distance of more than about 50 mm through a metal probe portion having a temperature within 700 C. degrees of the temperature of the melt.

It has been found that, whilst ultrasound pulses will travel readily through iron and other metals at room temperatures and slightly elevated temperatures, the metals, especially iron, absorb (or attenuate) very large amounts of sound energy when they are at temperatures approaching their melting points. Consequently, a steel probe having one end protruding into molten steel rapidly attains a temperature at which it attenuates so much of the sound energy reflections from the melt that useful analytical information cannot be obtained. Accordingly, the present invention provides a novel form of such probe, in which the path of travel of the sound reflections through metal at these very high temperatures is reduced to an acceptably small length, to allow useful signals to be obtained therefrom. This is accomplished by providing an effective cooling means in the probe, at a position close to the melt-penetrating end thereof.

As noted, a probe according to the present invention is effectively cooled so as to provide a pathway for the ultrasound reflection therethrough, in use, which is not longer than about 50 mm in metal having a temperature no more than 700 C. degrees different from the temperature of the melt. Thus, in the case of a steel melt, at its usual temperature of about 1470-1480 C., or higher, the temperature of the metal probe at a distance of 50 mm or more from the point of contact with the melt should be 770 C. or lower. These figures are based on a steel probe of cylindrical shape and 25 mm cross-sectional diameter, which is effectively about the smallest practical diameter of probe which can be used to put enough sound energy into the melt for practical purposes. These figures must of course be related to the limits of conductivity of the material from which the rod is constructed, and to the chosen diameter of the rod. The heat flow (H) along a length of conductive material is given by the equation:

$$H = KA(T_2 - T_1)/L$$

wherein K is the specific conductivity of the material, L is the length of the conductor over which the heat flow is to be measured, $T_1$ and $T_2$ are the temperatures at the ends of the length and A is the cross-sectional area. By use of this expression and the figures given above, one can readily calculate the appropriate required temperature gradient, and necessary cooled temperatures at distances along the probe, for a probe of different material and size, and melts of different temperatures.

The means by which the cooling of the probe is accomplished is not critical, provided the necessary degree of cooling at the required location is obtained. Preferred according to the present invention is the circulation of a cooling gas or liquid through a zone of the probe adjacent to the melt-contacting tip thereof.

Most suitably, a high pressure water flow jacket is arranged to provide water flow over the metal of the probe, at a rate sufficient to effect the necessary cooling. The jacket provides a cooling zone close to the liquid metal interface, e.g. at 100–115 mm from the interface. Water pressures of the order of 825 kPa and water flow rates of up to 2 l/sec may be used. The water jacket should be designed to withstand these conditions and avoid leakages, especially because it is being used in the vicinity of liquid steel. The probe design including the water jacket should also provide good acoustic transmission.

For cooling, liquid helium, nitrogen or other inert material is suitable and may be used. Other, less drastic cooling means may be employed in addition, at locations further spaced from the melt-contacting tip, to assist the necessary cooling of the probe, to provide the required temperature gradient. For example, water or other coolant liquid is circulated through, say, a water jacket or threads or bores in the main part of the probe rod.

A probe according to the present invention is thus capable of inputting ultrasound pulses to a batch of molten metal which it contacts, and receiving reflected sound therefrom, for analysis to determine composition, homogeneity, etc. It can also be used for ultrasound treatment of batches of molten liquid metal, since it is capable of transmitting high energy ultrasound pulses thereto, through its cooled melt-contacting tip. Such ultrasound treatment can be useful in dispersing inhomogeneities, and in causing coalescence of particles of impurities in the melt, to form particles which are large enough to rise to the top of a melt, and which can then be skimmed off. To accomplish this, however, very high energy ultrasound input is often required. A probe according to the invention allows this.

The invention will now be described by way of example with reference to the accompanying drawings, in which.

Figure 1:
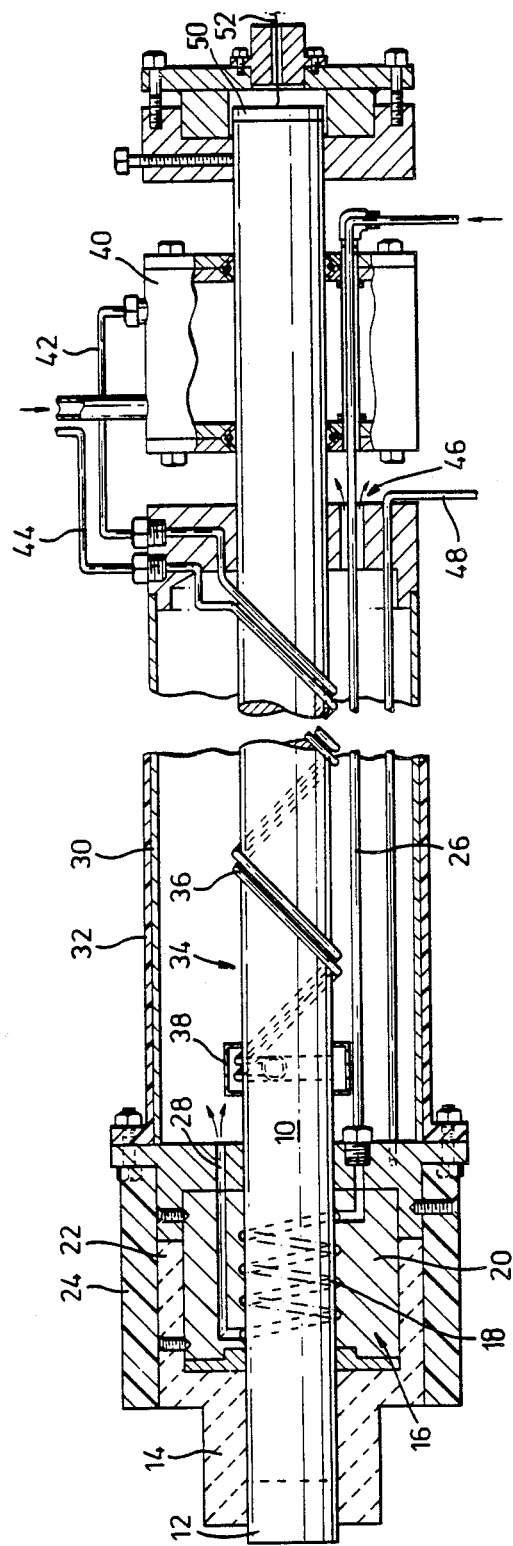
FIG. 1 is a diagrammatic view, partly in section, of a probe according to the present invention.

FIG. 1 shows a probe which has a core 10, e.g. of mild steel, in the form of cylindrical rod about 25 mm in diameter. The core 10 has a tip 12 for insertion into a, say, steel melt. The tip 12 is surrounded by a cylindrical shield 14, e.g. of boron nitride.

Upstream from the tip 12, a distance of about 50 mm, a cooling station generally designated 16 comprises a helical groove or coil 18 surrounding the core 10. The groove 18 is cut into the inner surface of a sleeve 20, e.g. of graphite or titanium, which overlies the core 10. Liquid circulated through the groove 18 thus makes direct contact with the core 10. The sleeve 20 is received within an enlarged portion 22 of the shield 14. Overlying the cooling station assembly is an outer cylindrical sleeve 24, e.g. of silicon, so that the cooling station as a whole is appropriately insulated.

An inlet pipe 26 is in communication with one end of the groove 18, and through which cooling fluid such as liquid helium or liquid nitrogen can be supplied to one end of the groove 18. Cooling fluid is vented through and outlet pipe 28, after passing through the groove 18, to the annular space surrounding the core 12.

Upstream of the cooling station 16, the probe is provided with an outer cylindrical steel casing 30 within an insulating sleeve 32, leaving an annular space surrounding the upstream portion of the core 10. A secondary cooling location generally designated 34, upstream from the cooling station 16, comprises a wide pitch cylindrical coil 36 over the cylindrical core 10, and terminating in a cylindrical reservoir 38. Water can be circulated through the coil 36 and reservoir 38, entering from a water jacket 40 provided further upstream on the probe, via an inlet pipe 42, and exiting via an outlet pipe 44 from the coil 36. The annular space between the steel casing 30 and the core 10 is vented to atmosphere as shown at 46, and contains an additional pipe inlet 48 for the supply of additional cooling fluid to the space itself.

At its upstream end, the probe is provided with a piezoelectric crystal 50, in contact with the core 10, with appropriate electrical connections 52. The crystal 50 provides ultrasound input to the core 10 from an electrical power supply, and electrical signals as a result of reflected sound pulses travelling up the core 10.

In operation, the tip 12 protrudes into the crucible or ladle of molten steel, either through a side port therein or into the top of the melt. The melt is normally at a temperature of about 1480 C. or above. The end of the boron nitride sleeve 14 also protrudes into the melt, so that the cooling station 16 is typically 25 to 38 mm from the melt. Liquid helium or other cooling liquid is supplied to the groove 18, via inlet pipe 26, and water is supplied both to water jacket 40 and to coil 36, to effect the necessary cooling. Very rapidly, the tip 12 rises to the temperature of the melt. However, at a distance 25 to 38 mm from contact with the melt, the probe 10 is at a temperature of about 750 C. as sensed by an appropriately located thermo-couple. The tip 12 starts to melt, brazing flux thereon having provided initially good interface contact by wetting, and ultrasound pulses are sent down the rod 10 from the piezoelectric crystal 50. Reflected sound from the melt travels back up the core 10, having only a very short length of travel from the tip 12 to the cooling station 16, at high temperature. The reflected sound signals are picked up by the piezoelectric crystal 50 and submitted via electrical connections 52 for analysis.

As the process continues, with the probe disposed upright, the tip 12 starts to melt away into the body portion within the ceramic sleeve 14. The tip is however immediately rebuilt, by solidification of metal from the melt onto the end of the tip. The position of the interface therefore stabilises within the sleeve 14. Provided that the sleeve does not crack and allow air to flow in, the interface will remain stable. Should air enter, it is likely that the interface will break and that a metal-gas interface will form, to hinder sound transmission.

When a probe is used in a horizontal disposition, protruding into a liquid melt, the hydrostatic pressure of the melt head will tend to maintain the interface. Any cracking of the ceramic sleeve may cause the melt to leak around the ceramic material, possibly giving rise to dangerous conditions.

Figure 2:
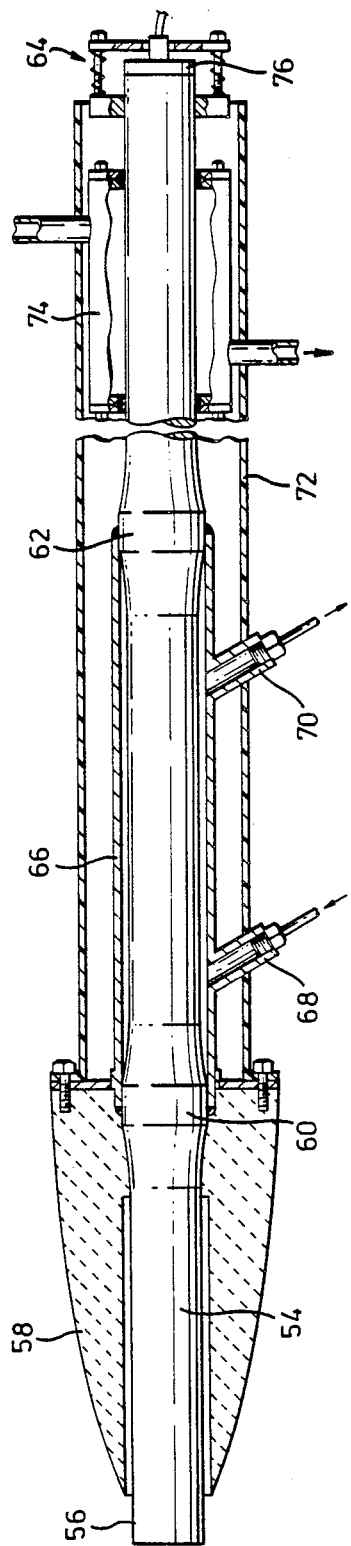
FIG. 2 is a sectional view of an alternative form of a probe according to the invention.

FIG. 2 shows an alternative form of probe having the same basic characteristics as that of FIG. 1, but equipped with a high pressure water jacket to provide the primary cooling station. The probe core 54 is made of low carbon steel or pure iron, with an overall length of about 600 mm and a main diameter of about 25 mm. As in the FIG. 1 embodiment, the melt-contacting tip 56 of core 54 protrudes from a surrounding ceramic sleeve 58, e.g. of boron nitride.

Along the length of the core 54, there are two thickened portions 60, 62 about 12 mm wide and having a maximum diameter about 30 mm. They are positioned respectively about 450 mm and 250 mm from the non-melt-contacting end 64 of the probe. They are machined in the core 54 so that the transition in diameter from 25 to 30 mm, on both sides, follows the contours of an acoustic trumpet, the changing slope being governed by an exponential relationship.

A cylindrical cooling jacket 66 having an inlet connection 68 and an outlet connection 70 is welded into place on the portions 60, 62, to provide a leak-proof cooling space in which the high pressure cooling water may make direct contact with the probe. An outer insulating sleeve 72 overlies the cooling jacket. A secondary cooling station, comprising a jacket 74 for cooling fluid circulation therethrough, is near the non-melt-contacting end 64. A piezoelectric crystal 76 with appropriate electrical connection is provided at the end 64.

Experiments have shown that such a design can hold the interface stable at a distance of about 115 mm from the cooling jacket 66, for long periods. The trumpet-shapes of the enlarged portion ensure that a welding operation, to seal the cooling jacket 66 in place, can be effectively performed without causing interference with the acoustic transmission properties of the probe.

Figure 3:
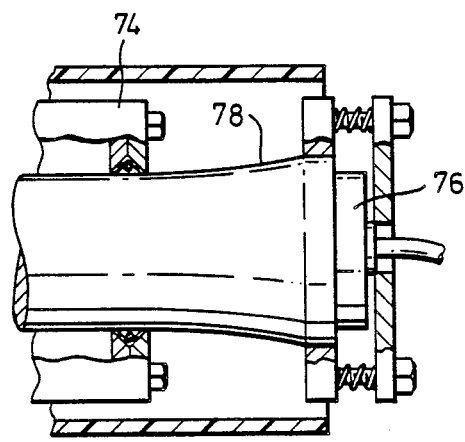
FIG. 3 shows a modification of the probe of FIG. 2.

FIG. 3 illustrates a modified non-melt-contacting end for a probe of FIG. 2. In this embodiment, the end 78 of the core 54 is in the shape of an acoustic trumpet, with exponentially-curved side-walls; they accommodate on the end surface thereof a larger and more powerful piezoelectric crystal 76, for supplying larger amounts of energy to the melt.

Each device illustrated in FIGS. 1, 2 and 3 is designed for use as a single probe, into a melt, both for transmission of ultrasound therein and reception of sound signals therefrom. It will of course be appreciated that in some circumstances it may be preferable to use two probes, one for transmission of signals into the melt and a second for reception of signals therefrom, each probe having its own piezoelectric crystal. In such cases, it is more important to provide the reflection signal receiving probe with the cooling means as described and defined herein, for maximum reception of reflected signals for analysis, but it is preferred that both probes should be so equipped and operated.

Figure 4:
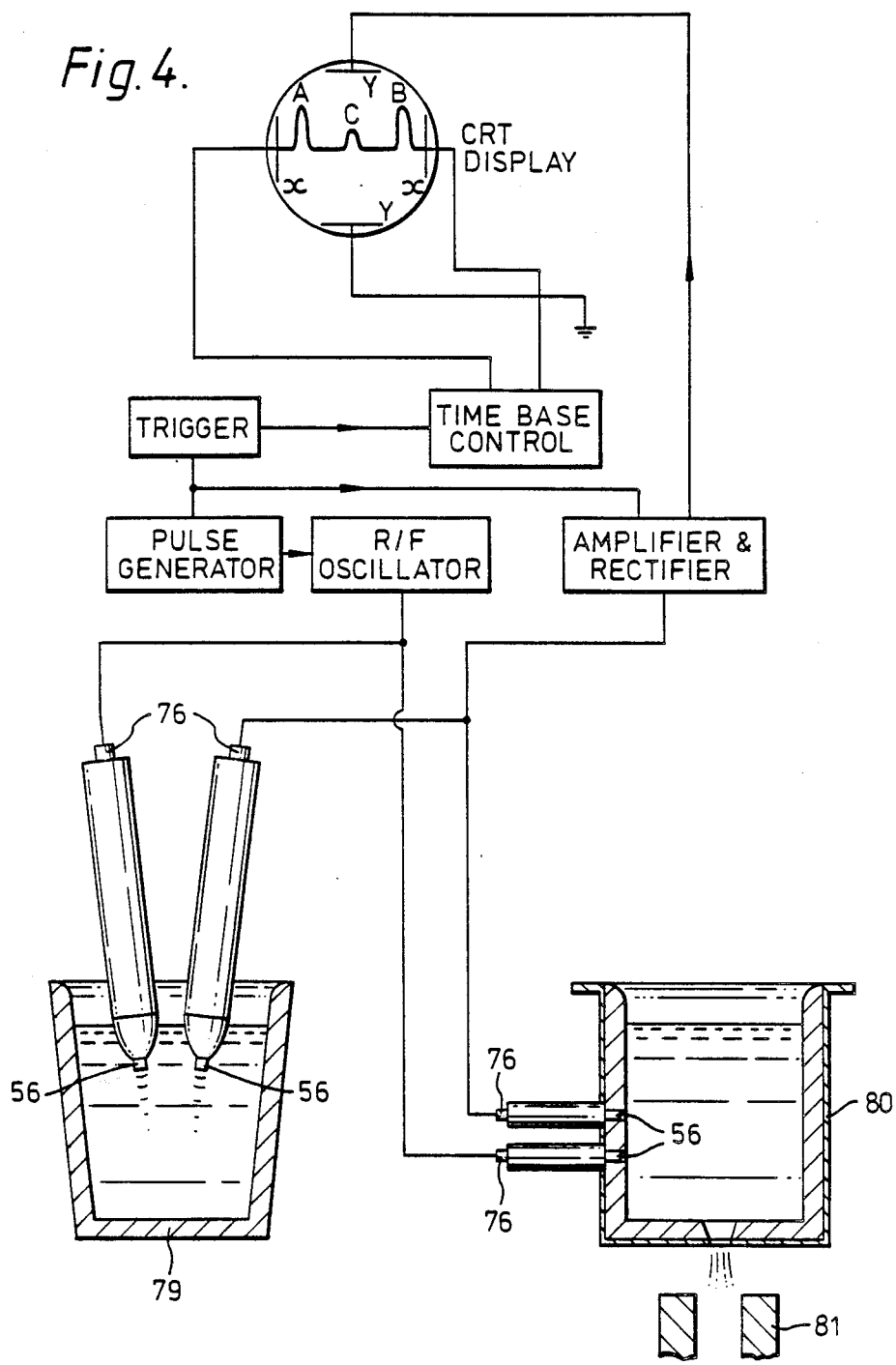
FIG. 4 is a diagrammatic illustration of apparatus for using the probe of FIG. 1.

FIG. 4 of the accompanying drawings is a diagrammatic illustration of a block diagram for a pulse-echo ultrasonic testing technique for use with the probe as described herein. This is generally an arrangement according to the prior art, but useful in connection with the improved probe of the present invention. In the form illustrated in FIG. 4, separate probes are designated, having respective transmitting crystals and receiving crystals, for the supplied ultrasound pulses and the received sound reflections. FIG. 4 indicates the use of alternative arrangements, namely vertically-disposed probes testing or treating a melt in a ladle 79, and horizontally-disposed probes testing or treating a melt in a tundish 80, from which the melt is fed to a mould 81. The reflected signals as received are displayed on a cathode ray tube display, for suitable measurement and analysis of the impurities and inhomogeneities located within the melt.

The oscillograph of reflected ultrasound signals so displayed typically shows one or more peaks of large amplitude at its right-hand side, derived from ultrasound reflections from the bottom of the melt-containing vessel, and a series of peaks of lesser amplitude to the left, derived from ultrasound reflections from inhomogeneities or suspended impurity particles in the melt. The horizontal axis of the oscillograph is a time scale, and indicates the time lapse between transmission and reflection reception of an ultrasound signal, so that those reflections which have travelled farthest, i.e. those from the bottom of the melt, appear to the right on the oscillograph. The degree of purity of the melt may be determined from the amplitude of the ultrasound reflections from the bottom of the melt vessel. The greater the amount of impurity in the melt, the more incident ultrasound will be reflected from the impurities, so that a smaller amount of the incident ultrasound will reach and be reflected by the bottom of the melt vessel. Hence, the amplitude of the bottom reflections on the oscillograph gives an indication of the impurity level in the melt.

To utilise this indication in practice, calibration with a melt of known purity level is first conducted. A gate is applied to the time base, and the change in amplitude of the bottom reflection signal is measured over the gated time period, and compared with the calibration figures to determine impurity levels in the melt under test.

In an alternative method, the number of impurity particles is counted, by counting the number of signal reflections from a given area and depth of the melt. Signal reflections appear on the time base of the oscillograph, according to the depth of the particle responsible for the reflection. By computer counting and conversion, assuming the test area of the melt to be representative, the number of impurity particles present can thus be computed.

Separate probes for transmission and reception are of more importance for use with aluminium probes and aluminium melts, according to the present invention. The acoustic impedance of aluminium is relatively high, so that attempts to use a single probe to conduct both downgoing signals and upcoming signals leads to excessive attenuation of sound within the probe. More detailed and accurate measurements are accordingly obtainable using two probes in such circumstances, at the expense of apparatus inconvenience.

It is also preferred, according to the present invention, to subject the reflected signals as received to computer analysis, rather than to display them on a cathode ray tube display for analytical purposes. A computer can be arranged to take readings and measurements of the reflected sound at given intervals of time, and, by suitable programming, to compare the signals received at different times. This enables an operator to tell whether the detected inhomogeneities are moving within the melt or whether they are stationary, at fixed positions therein. This can be of considerable importance, especially when a melt is being treated with high energy ultrasound in order to improve its characteristics. Computer analysis of the readings can then indicate, for example, whether impurities are being driven to the surface of the melt, whether cavities and voids therein are being filled and air bubbles driven to the surface of the melt, or whether particles are being caused to coalesce or are being more finely broken down.

A difficulty commonly encountered in ultrasound testing and treatment of melts is the obtaining of sufficiently deep penetration of the ultrasound into the melt, both to obtain ultrasound reflections from the bottom and throughout the depth of the melt for analysis, and to effect ultrasound treatment of the melt throughout its volume. The most troublesome impurity particles in a ferrous melt are particles which are less dense than molten steel, such as silicates and oxides. Provided that the particles are large enough (e.g. 200 $\mu$m or above), they will float to the top of a ferrous melt for removal by, for example, skimming or bottom pouring. The present invention provides a method by which impurity particles in a ferrous or aluminium melt can be caused to coalesce to a size sufficiently large that they float to the melt surface, for removal therefrom, utilising long pulsed ultrasound.

In this method, pulsed ultrasound is supplied to a metal melt through a side inlet into the vessel, e.g. substantially horizontally. This is conveniently accomplished by using a probe of the invention, as described above. By expanding the area of the upstream end of the probe core as a bell-shaped or "trumpet" end, with exponentially curved upstream side-walls, a bigger and more powerful piezoelectric crystal can be accommodated, e.g. of the type illustrated in FIG. 3, for supplying greater amounts of pulsed ultrasound energy to the melt.

In addition to its use as described above for analysis and determination of impurities in melts, a probe according to the invention, substantially horizontally mounted in a melt-containing vessel, can be used to treat melts with pulsed ultrasound. In a preferred method according to the invention, this is accomplished by creating a standing ultrasound wave in the melt. It has been found that impurity particles in the melt concentrate into the nodes (non-vibration areas) of the melt under such standing wave conditions. The impurity particles can coalesce in such areas and form particles large enough to rise to the melt surface, for removal therefrom. Then, by the use of a conventional horizontal casting mould located in the vicinity of the ultrasound treatment in the melt, a rod of substantially impurity free metal can be withdrawn from the melt in conventional manner.

Figure 5:
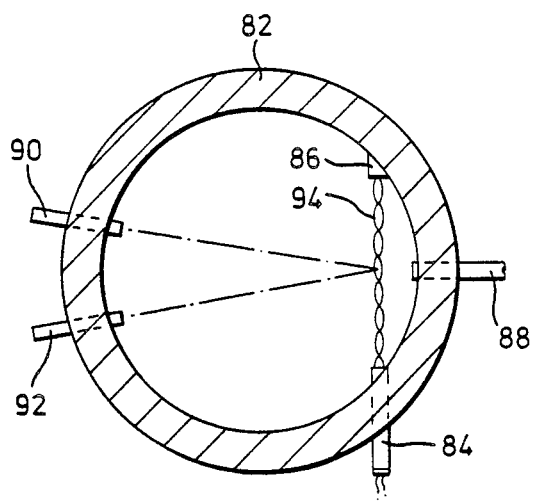
FIG. 5 is a plan view, partly in section, of a melt-containing vessel equipped with probes according to the invention, in horizontal disposition for melt treatment therewith.

This treatment and purification process is diagramatically illustrated in FIG. 5. A vessel 82 (which can contain a melt) is provided with a first ultrasound emitting probe 84, which may be of the form illustrated in FIG. 1 or FIG. 2, although this form is not essential since it is not required to receive reflected ultrasound signals. Opposite to the probe 84 is an ultrasound reflecting means 86 such as a refractory brick. A horizontal casting mould 88 is located between the probe 84 and the reflector 86 and at substantially the same horizontal level in the vessel 82.

At a position generally diametrically opposite to the casting mould 88 and at the same horizontal level in the vessel 82 as the probe 84 and reflector 86, there are a second ultrasound emitting probe 90 and an ultrasound receiving probe 92. These are both conveniently of the form illustrated in FIG. 2.

In operation, ultrasound from the first probe 84 is reflected from the reflector 86. By suitable tuning of the ultrasound frequency and/or adjustment of the melt temperature, a standing wave 94 is established in the melt between the first probe 84 and the reflector 86. Ultrasound emitted from the second probe 90 and received by the receiving probe 92 is used to determine the presence of the standing wave 94, by showing the presence of concentrations of impurity particles in regular patterns at the appropriate distance from the probes 90 and 92, corresponding to their distance from the first probe 84. As the process continues, the distance between the first probe 84 and the reflector 86 changes, owing to the melting of the tip of probe 84 in contact with the melt. This causes disruption and loss of the standing wave 94. When this is detected by the second probe 90 and the receiving probe 92, adjustments to the frequency of the ultrasound emitted from first probe 84 are made to restore the standing wave.

The inhomogeneous particles thus concentrate at the nodes of the standing wave 94, coalesce and rise through the body of the melt. A rod of substantially pure metal can now be cast and withdrawn from the melt, from the vicinity of the standing wave, using the horizontal casting mould 88 in conventional manner. In this way, cast metal, ferrous, aluminium or other, of increased purity, can be obtained as a result of ultrasound treatment.

I claim:

1. A probe for ultrasound testing or treatment of a molten metal, which comprises:
    an ultrasound-transmitting rod of which one end is downstream and adapted to contact molten metal under test or treatment, said rod being formed from the same metal as the molten metal to be tested;
    an insulating sleeve surrounding said downstream end of the rod, said sleeve being capable of withstanding the temperature of said molten metal and preventing air from contacting said downstream end of the rod when said downstream end is in contact with said molten metal, said sleeve allowing said downstream end of the rod to melt when immersed in said molten metal and subsequently to solidify within said sleeve when said probe is in use;
    a piezoelectric crystal adapted to supply ultrasound to or receive ultrasound from the rod;
    first rod-cooling means located adjacent the downstream end of the rod and being operable to create in the rod a steep temperature gradient at least equivalent to 700° C. over a length of 50 mm from the point of contact of the downstream end of the rod with the molten metal, for a cylindrical rod 25 mm in diameter such that said downstream end melts and quickly solidifies within said sleeve to establish a stable liquid-solid interface; and
    second rod-cooling means disposed above said first rod-cooling means and being operable to cool substantially the remainder of the rod.

2. A probe according to claim 1, wherein the downstream end of the ultrasound-transmitting rod is surrounded by a highly heat-resistant shield.

3. A probe according to claim 1, wherein the upstream end of the ultrasound-transmitting rod is enlarged, in the form of an acoustic trumpet.

4. A probe according to claim 1, wherein the first rod-cooling means comprises a reservoir, for cooling fluid, in contact with the surface of the rod.

5. A probe according to claim 4, wherein the reservoir comprises an annular chamber around the rod, through which fluid can be circulated under high pressure and at a high rate.

6. A probe according to claim 5, wherein the chamber is defined by a jacket fixed to protrusions on the ultrasound-transmitting rod.

7. A probe according to claim 6, wherein the protrusions are integral with the ultrasound-transmitting rod and have forward and rearward acoustic trumpet-shaped side-walls exponentially curved to minimise acoustic transmission interference.

8. A method of testing a molten metal, which comprises:
   contacting the molten metal with one end of an ultrasound probe made of a ferrous metal the same as said molten metal;
   inhibiting air from contacting the one end of the probe;
   cooling the probe at the one end of the probe to create therein a steep temperature gradient such that a length of the probe not greater than 50 mm from its point of contact with the molten metal has a temperature within 700 ° C. of the temperature of the molten metal to allow a stable liquid-solid interface between the one end of the probe and the molten metal to be established;
   supplying pulsed ultrasound to the molten metal; and
   analyzing reflected ultrasound received at the probe to detect inhomogeneities and the like in the molten metal.

9. A method according to claim 8, wherein cooling is achieved by circulation of high pressure water in contact with the surface of the probe.

10. A method according to claim 8, in which ultrasound is supplied to the melt through the probe.

11. A probe for ultrasound testing and treatment of molten steel comprising;
   a steel ultrasound-transmitting rod having a downstream end adapted to contact molten steel under test or treatment;
   an insulating sleeve surrounding said downstream end of the rod, said sleeve being capable of withstanding the temperature of said molten metal and preventing air from contacting said downstream end of the rod when said downstream end is in contact with said molten metal, said sleeve allowing said downstream end of the rod to melt when immersed in said molten metal and subsequently to solidify within said sleeve when said probe is in use;
   a piezoelectric crystal on said rod adapted for connection to supply ultrasound to or receive ultrasound from said rod;
   first rod-cooling means located adjacent said downstream end and being operable to cool the downstream end of the rod to create herein a temperature gradient at least equivalent to that created in such a rod of about 25 mm in diameter and made of steel and contacting the melt at melt temperature and having a temperature of about 700° C. lower than said melt temperature at a location of about 50 mm from the point of contact of the melt such that said downstream end melts and quickly solidifies within said sleeve to establish a stable liquid-solid interface; and
   second rod-cooling means disposed above the first rod cooling means and being operable to cool substantially the remainder of the rod.

12. The probe of claim 11 wherein said probe is made of mild steel.

13. A method of testing molten steel comprising:
   contacting the molten steel with one end of an ultrasound probe made of steel;
   inhibiting air from contacting the one end of the probe;
   cooling the probe at the one end of the probe to create therein a steep temperature gradient such that a length of the probe not greater than 50 mm from its point of contact with the molten steel has a temperature within 700° C. of the temperature of the molten steel to allow a stable liquid-solid interface between the one end of the probe and the molten steel to be established;
   supplying pulsed ultrasound to the molten steel; and
   analyzing reflected ultrasound received at the probe to detect inhomogeneities and the like in the molten steel.

* * * * *